June 30, 1942. W. E. LAMMERTS Plant Pat. 529
PEACH TREE
Filed Sept. 20, 1941
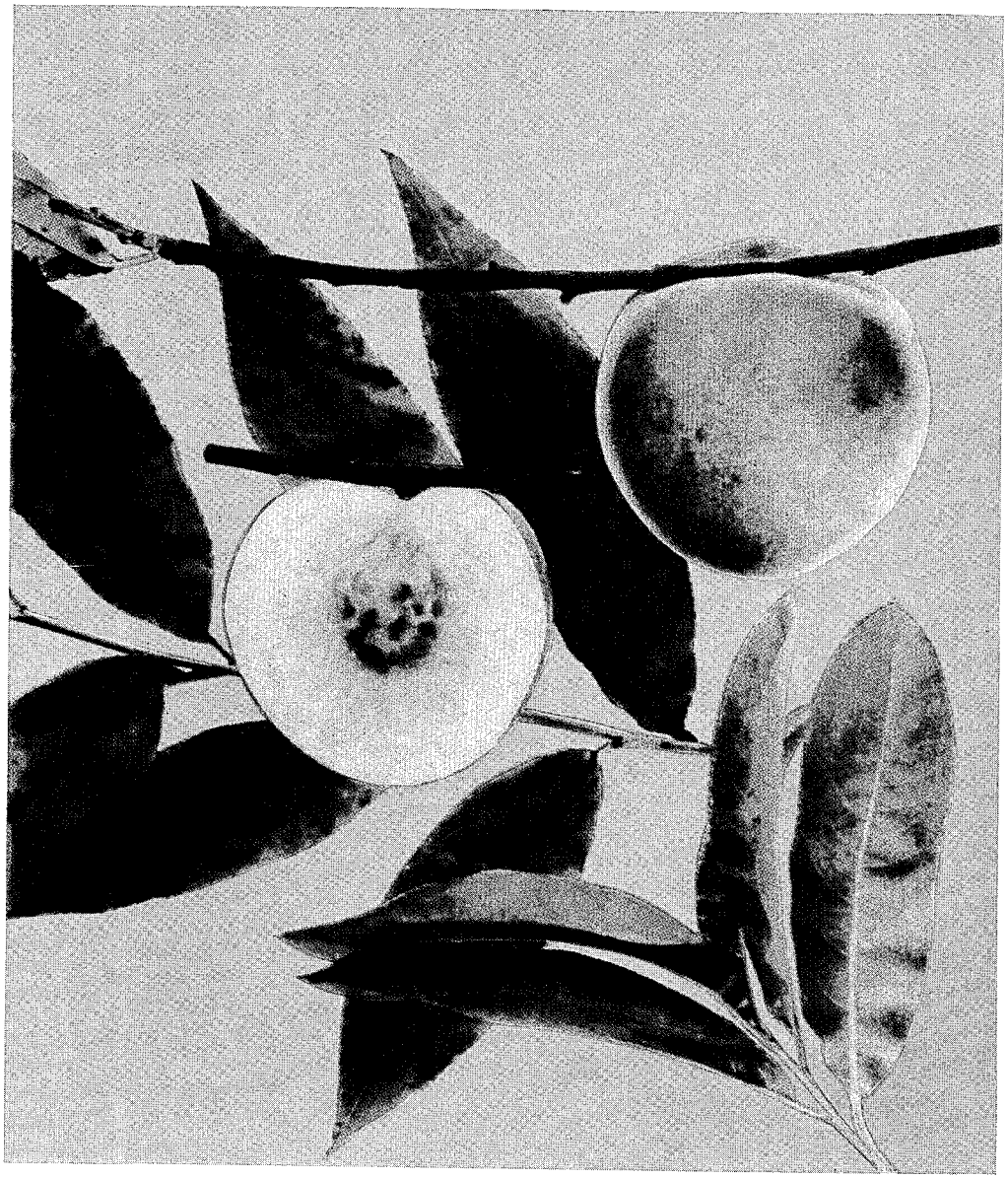
Inventor
W. E. Lammerts
By Robb & Robb
Attorneys Patented June 30, 1942

Plant Pat. 529

UNITED STATES PATENT OFFICE

529

PEACH TREE

Walter E. Lammerts, Ontario, Calif., assignor to Armstrong Nurseries, Inc., Ontario, Calif., a corporation of California Application September 20, 1941, Serial No. 411,715

1 Claim. (Cl. 47—62)

The present invention relates to a new and distinct variety of peach tree, the result of a definite effort to obtain the combination of early ripening and high coloring of the skin.

It is well known that the attractiveness of fruit greatly affects the sale value of such fruit, but the difficulty with the known early ripening varieties that may possess to some degree this high color is that in such sections of this country, such as southern California, the predominating mildness of the winters seems to interfere with a satisfactory crop. Reference in this connection is made to the early ripening varieties "Mayflower," "Vainqueur" and "Alexander," and to the fact that these varieties are almost entirely without red or pink coloring, having instead predominantly green skin.

To obtain the desired combination of high and beautiful skin color and earliness of ripening, I, therefore, pollinated the pistils of the known variety "Babcock" with the "Mayflower" peach pollen. The result of this cross pollination is found in the new variety set forth herein, the ripening period being comparable to that of the "Mayflower" variety but the color being far superior to that of the "Mayflower." The early ripening and its resistance to delayed foliation are similar to the variety "Babcock," which the new variety resembles in color and flavor. It may be noted, however, that the "Babcock" variety does not ripen for approximately six weeks after this new variety and therein lies the important distinction between the latter and the variety "Babcock."

This peach variety was bred especially for warm climates, such as experienced in southern California and Arizona, and its value, generally speaking, is found in the fact that said new variety bears crops regularly each year regardless of the mildness of the preceding winter.

For purposes of comparison, it is noted that the new variety of peach ripened at Ontario, California, about the 25th day of May after a winter during which three hundred hours of temperatures at 40° F., or below, were experienced between November 15 and the succeeding January 15; whereas the variety "Mayflower," the male parent of this new variety, and heretofore the earliest variety to ripen (when as much as twelve hundred hours of 40° F. were experienced) did not ripen under conditions stated above until June 15, and had a very light crop of poor quality fruit.

In addition to the main characteristics above referred to, the following detailed description sets forth further desirable qualities and features, all reference to color being in accord with Ridgway's Color Standard:

Seedling:
- Male parent.—"Mayflower."
- Female parent.—"Babcock."

Dates of first and last picking: May 25 and June 4 (season of 1941).

Tree: Medium large; medium vigorous; upright; spreading; open; vase-formed; hardiness (bred for warm climate); very productive; regular bearer.

- *Trunk.*—Medium stocky; smooth (as to young trees up to 1¾ inches diameter).
- *Branches.*—Medium to slender; smooth; near Chocolate, Plate XXVIII, on ⅜" to ½" caliper branches; dull. *Lenticels*—medium numerous; medium large.
- *Leaves.*—Length—3 to 4 inches. Width—1⅛ to 1½ inches. Medium large; ovate; lanceolate near base to lanceolate toward tip; acutely pointed; medium thick; near Cress Green, Plate XXXI, above and near Biscay Green, Plate XVII, beneath; smooth. *Margin* — glandular. Average number of glands approximately 120. Finely serrate. *Petiole*—short; medium thickness. *Glands* — average number — usually two, sometimes one, and sometimes wanting. Usually opposite; medium to small; globose. Position—on each side of petiole slightly encroaching on leaf margin. *Stipules*—early deciduous, about ¼ inch long, lanceolate, margins lined with stout stipitate glands of differing sizes.
- *Flower-buds.*—Hardiness (bred for warm climate); large; long; conic; pointed; free; pubescent.
- *Flowers.*—Dates first and full bloom. *First bloom*—about February 25. *Full bloom*—about March 5. Early compared with other varieties. Very large; pink.

Fruit: Maturity when described—eating hard under ripe about June 4.

- *Size,*—Fairly uniform; medium to small. Diameter axial—2 to 2½ inches. Transverse in suture plane—1⅞ to 2⅜ inches. At right angles to suture plane—1⅞ to 2⅜ inches.
- *Form.*—Uniform; symmetrical; globose.
- *Suture.*—An inconspicuous line; shallow; extends from base to beyond but discontinuous at apex.

*Ventral surface.*—Sounded strongly, only slightly lipped toward apex. *Lips*—equal.

*Cavity.*—Rounded, almost circular; slightly elongated in suture plane. *Depth*—approximately ⅝ inch. *Breadth*—¾ inch. *Markings*—none.

*Base.*—Cuneate.

*Apex.*—Short; rounded. *Pistil point*—rarely identifiable.

*Stem.*—Length—⅛ inch. Medium to stout; glabrous. *Adherence to stone*—strong to medium.

*Skin.*—Thin; tender; free when fully ripe. *Tendency to crack*—none in dry season. *Color*—skin color—basic color near Pale Greenish Yellow, Plate V, near stem end to near Maize Yellow, Plate IV, toward apex on some to Sulphur Yellow, Plate V, on others. Usually dotted with Ox-Blood Red, Plate I, on one side and striped with Ox-Blood Red, Plate I, at points on one side and at other places on same side mottled with Begonia Rose, Plate I. The other side and sometimes the whole Peach when fully exposed to sun is usually slightly darker than Ox-Blood Red, Plate I, with faint stripes of Victoria Lake, Plate I. *Down*—abundant; short; does not roll up when rubbed, but will separate from skin.

Flesh:

*Color.*—Flesh color—near Pale Viridine Yellow, Plate V, near pit; between Sulphur Yellow, Plate V, and White, Plate LIII, near skin. *Surface of pit cavity*—Pale Viridine Yellow, Plate V.

*Amygdalin.*—Moderate. *Juice* — abundant; rich.

*Texture.*—Firm; fine; melting.

*Fibres.*—Few; fine; tender.

*Ripens.*—Even.

*Flavor.*—Mild, and sweet with slight acid.

*Aroma.*—Pronounced.

*Eating quality.*—Good.

Stone: Semi-cling Adheres to flesh over entire surface when firm and over upper half of sides when fully ripe.

*Fibres.*—Short; stout; retains short fibre-like threads in each depression of pit when peach very ripe.

*Size.*—Small.

*Length.*—One inch.

*Breadth.*—¾ inch.

*Thickness.*—⅝ inch.

*Form.*—Nearly oval; full toward base and apex.

*Base.*—Broad and rounded. *Hilum*—oval. *Apex*—usually rounded

*Sides.*—Nearly equal; usually curved on right and left sides.

*Surface.*—Pitted throughout, although more lightly toward center of sides.

*Ridges.*—Rounded; slightly jagged toward apex.

*Embryo.*—Elongated; very thin.

*Pits.*—Ventral edge.—Thick with wing throughout.

*Dorsal edge.*—Full with shallow, narrow groove toward base to above center. *Ridges* on either side—continuous on ventral edge but interrupted on dorsal edge.

*Color of stone.*—When dry, Pinkish Cinnamon, Plate XXIX, to Cinnamon, Plate XXIX.

*Tendency to split.*—None.

Use: Market; local; dessert.

Keeping quality: Medium good.

Resistance to:

*Insects.*—Medium good.

*Diseases.*—Medium good.

Shipping quality: Medium good.

I claim:

A new and distinct variety of peach characterized as to novelty by its early ripening and the high skin coloring of its fruit; the resistance to delayed foliation in mild winter climates; and uniform production annually of satisfactory crops, substantially as shown and described.

WALTER E. LAMMERTS.